United States Patent [19]
Berg

[11] Patent Number: 6,132,709
[45] Date of Patent: *Oct. 17, 2000

[54] **BACTERIN FOR THE TREATMENT OF *NECROPHORUM* DISEASES AND A METHOD FOR THE PRODUCTION THEREOF**

[75] Inventor: John N. Berg, Columbia, Mo.

[73] Assignee: Bayer Corporation, Pittsburgh, Pa.

[*] Notice: This patent issued on a continued prosecution application filed under 37 CFR 1.53(d), and is subject to the twenty year patent term provisions of 35 U.S.C. 154(a)(2).

[21] Appl. No.: 07/825,465

[22] Filed: Jan. 24, 1992

Related U.S. Application Data

[63] Continuation of application No. 07/534,894, Jun. 7, 1990, abandoned.

[51] Int. Cl.$^7$ .................................................. A01N 63/00
[52] U.S. Cl. .................... 424/93.4; 435/243; 435/245; 435/252.1
[58] Field of Search ................... 424/93.4; 435/243, 435/252.1, 822, 245

[56] References Cited

U.S. PATENT DOCUMENTS 4,061,751  12/1977  Adam ....................................... 424/250
4,203,968  5/1980  Harris et al. ............................... 424/92

FOREIGN PATENT DOCUMENTS 984293  2/1976  Canada .
310317  4/1989  European Pat. Off. .
2174745  10/1973  France .

OTHER PUBLICATIONS

Garcia et al, "Biological Characterization of *Fusobacterium necrophorum* Cell Fractions in Preparation for Toxin and Immunization Studies", Infection and Immunity, Apr., 1975, pp. 609–616.

Abe et al, "Immunization of Mice Against *Fusobacterium necrophorum* Infection by Parenteral or Oral Administration of Vaccine", Am. J. Vet. Res., vol. 39, No. 1, pp. 115–118, Jan., 1978.

Synthea Mass, The Immune Responses of Mice and Cattle to *Fusobacterium necrophorum*, Aug. 1986.

John William Evans, Jr., Serological Investigations of *Fusobacterium necrophorum*, (Dec. 1983).

Biosis Previews Database Biosis, Phila., PA., Clark, B.L. et al, "Studies into Immunization of Cattle Against Interdigital Necrobacillosis", Abstract Nb: 82053868 and Aust. Vet. J., vol. 63 No. 4, 1986 pp. 107–110.

Kaititch, "Etude Comparative Sur La Valeur Prophylactique de 2 Vaccins Contre Le Pietin Du Mouton", Bul. Soc. Vet. et Med. Comparee, vol. 76, No. 4 (Lyon 1974).

Am. J. Vet. Res. (1983), 44(9), 1789–92 Coden; Ajvrah; Issn; 0002–9645, Sep., 1983, C.M. Scanlan et al, Comparative biological features of a rat liver abscess model induced with three *Fusobacterium necrophorum*strains.

*Primary Examiner*—Leon B. Lankford, Jr.
*Attorney, Agent, or Firm*—Joseph C. Gil; Godfried R. Akorli

[57] ABSTRACT

A method for treating cattle and sheep to prevent foot rot and/or liver necrosis comprising administering a *Fusobacterium necrophorum* bacterin which is a β-propriolactone inactivated *Fusobacterium necrophorum* isolate to the animal being treated.

10 Claims, No Drawings

BACTERIN FOR THE TREATMENT OF *NECROPHORUM* DISEASES AND A METHOD FOR THE PRODUCTION THEREOF

This application is a continuation, of application Ser. No. 07/534,894 filed Jun. 7, 1990 now abandoned.

BACKGROUND OF THE INVENTION

The present invention relates to a *F. necrophorum* bacterin, to a process for the production thereof and to a method of treating Fusobacterium disease with this bacterin.

*Fusobacterium necrophorum* (formerly referred to as *Sphaerophorus necrophorus*) is an obligate anaerobic gram negative rod, which is generally recognized as playing a significant role in a variety of disease entities affecting ruminants including Chronic Footrot in sheep, Acute and Chronic Footrot in cattle, Liver Abscess in cattle, and Diphtheria in calves.

Garcia et al discloses in "Biological Characterization of *Fusobacterium necrophorum* Cell Fractions in Preparation for Toxin and Immunization Studies", *Infection and Immunity*, April 1975, pages 609–616, that preliminary trials indicated that an alum-precipitated toxoid derived from the cytoplasm of bovine liver abscesses reduced liver abscesses to a level of 10% as compared to the 35% level of the control sample.

Abe et al discloses in "Immunization of Mice Against *Fusobacterium necrophorum* Infection by Parenteral or Oral Administration of Vaccine", *Am. J. Vet. Res.*, Vol. 39, No. 1, pages 115–118 (January 1978) a vaccine made with whole cell suspensions of formalin-killed *F. necrophorum*. This vaccine was administered by three different routes: intraperitoneal injection of the killed cells in a saline solution, intraperitoneal injection of the killed cells with added aluminum hydroxide adjuvant and by feeding as a powder to which lyophilized bacterial cells had been added. However, even the most effective treatment (i.e., IP injection of cells plus adjuvant) resulted in mortality rates of almost 40% after seven days post challenge. These bacterins have not, however, shown sufficient efficacy when tested under field conditions to be of commercial value.

Katitch reports in "Etude comparative sur la valeur prophylactique de 2 vaccins contre le pietin du mouton", *Bull. Soc. Vet. et Med. comparee*, Vol. 76, No. 4 (Lyon 1974), the results of a comparison of two commercial vaccines against Foot-Rot in field studies. One of the vaccines contained only one antigen and was found to be almost completely ineffective. The second vaccine was a multiple antigen preparation in which *S. necrophorus, Staphylococcus pyogenes* and *W. perfringens* were included.

U.S. Pat. No. 4,061,751 discloses a treatment for foot rot and liver lesions in ruminant animals in which a 6-substituted 3-nitroimidazo[1,2-b]pyridazine is administered to the animal being treated. The preferred method of administration is oral administration.

To date, however, no effective prophylactic agent to control or prevent F. necrophorum diseases is commercially available.

SUMMARY OF THE INVENTION

It is an object of the present invention to provide a novel bacterin useful in the treatment of Fusobacterium disease.

It is also an object of the present invention to provide a process for the production of a *Fusobacterium necrophorum* bacterin which is effective in the prevention of footrot in sheep and cattle and liver necrosis in cattle.

It is a further object of the present invention to provide an inactivated *F. necrophorum* bacterin which provides significantly better protection against Fusobacterium disease than known treatments.

These and other objects which will be apparent to those skilled in the art are accomplished by inactivating a virulent isolate of *Fusobacterium necrophorum* with β-propriolactone. Any excess β-propriolactone may then be removed by hydrolysis. The inactivated bacterin may then be combined with a known adjuvant to produce a vaccine suitable for parenteral administration.

DETAILED DESCRIPTION OF THE PRESENT INVENTION

The present invention relates to a process for bacterin preparation in which β-propiolactone (BPL) is used to inactivate virulent *F. necrophorum* isolates. Residual BPL may be hydrolyzed and an adjuvant may then be added. The bacterin prepared by this process is useful in the prevention and control of *F. necrophorum* in ruminant animals such as sheep, goats and cattle under normal field conditions.

The present invention also relates to a β-propiolactone (BPL) killed bacterin prepared from virulent isolates of *Fusobacterium necrophorum* which is useful as an aid in protecting against diseases caused by *F. necrophorum* in cloven hoofed animals (i.e. cattle, sheep, goats, etc.). Examples of such diseases include Footrot, Liver Abscess, Calf Diphtheria, Interdigital Dermatitis, etc. Previous attempts at preparing efficacious bacterins using *Fusobacterium necrophorum* have been unsuccessful, probably due to the fact that critical antigens necessary for induction of immunity were not preserved by use of inactivation processes which involved heat or formaldehyde. Applicant has found, however, through challenge studies conducted in mice that BPL inactivated, adjuvanted cultures can protect mice against experimental challenge with heterologous isolates of *F. necrophorum*. Field challenge trials conducted in pregnant sheep and feedlot cattle have also shown that the BPL inactivated bacterin of the present invention is effective in reducing both incidence and severity of ovine and bovine Footrot.

The present invention can be practiced with any virulent isolate of *F. necrophorum*. A virulent isolate is one which is capable of producing a typical *F. necrophorum* lesion in cattle or sheep. Two isolates, designated 5118 and 5120 were isolated from Missouri sheep showing signs of chronic ovine Footrot and used in the development of the bacterin of the present invention. The present invention is not, however, limited to bacterins derived from these specific isolates because these isolates exhibited characteristics which are typical of all biovar (biotype) A of *F. necrophorum*. The characteristics relied upon to make this determination were cultural and virulence characteristics such as isolation from typical lesions, pathogenicity for mice, and growth as flat grayish colonies on blood agar. These known characteristics of *F. necrophorum* and techniques for determining them are disclosed in publications such as *Virulence Mechanisms of Bacterial Pathogens*, Roth, J (ed), Chap 21, p. 343–362, 350 "Approaches Virulence Determinants of Fusobacterium and Bacteroides spp" by David E. mery, (1988); *Footrot and Foot Abscess of Ruminants*, Egerton, J. R., Yong, W. K. & Rifkin, G. G., Chap. 4, pages 69–79, 70, "Foot Abscess of Cattle" by Clark, B. L. pages 69–79, 70 (CRC Press 1989).

The virulent *F. necrophorum* isolates used to produce the bacterins of the present invention may be grown in any of the growth media known to those in the art for periods of from about 10 hours to about 24 hours, preferably from about 16 to about 18 hours at temperatures of from about 35 to about 39° C., preferably from about 36 to about 38° C. Specific examples of suitable growth media include: Eugon broth (available from Baltimore Biological Laboratories (BBL)) supplemented with maltose, beef extract, yeast extract, menadione and l-cysteine-HCl; tryptic soy broth with dextrose (available from BBL) supplemented with beef extract and l-cysteine-HCl; and brain heart infusion broth (available from Difco) supplemented with yeast extract and l-cysteine-HCl. Preferred growth media are Brain Heart Infusion Broth supplemented with yeast extract and l-cysteine-HCl; and tryptic soy broth with dextrose supplemented with beef extract and l-cysteine-HCl. The most preferred growth medium is Brain Heart Infusion Broth (available commercially from Difco Labs or BBL) supplemented with l-cysteine hydrochloride and yeast extract.

The fermented cultures are then cooled to a temperature of from approximately 4 to approximately 10° C., preferably from about 4 to about 8° C., and most preferably from about 4 to about 7° C. The cooled cultures are then inactivated with β-propiolactone (BPL). The β-propiolactone is generally used in excess, typically in a quantity which is about 0.10 to about 0.15%, preferably about 0.11% v/v. In the inactivation procedure, the β-propriolactone is added directly to the cooled culture and the resultant mixture is allowed to stand for a period of at least 24 hours, preferably from about 48 to about 96 hours. The culture is maintained at a temperature of no more than 10° C., preferably from about 4 to about 7° C. during the inactivation stage of the process. Residual β-propiolactone may then be removed or inactivated by any of the known procedures. One suitable procedure which may be employed is hydrolysis. More specifically, the BPL-containing culture is heated to a temperature of at least 36° C., preferably from about 36 to about 38° C. and most preferably from about 30 to about 40° C. for a period of at least about 2 hours, preferably from about 3 to about 5 hours, and most preferably about four hours.

Known preservatives may then be added to the inactivated culture. Suitable preservatives include: thimerosal added to concentrations of up 1:1000, gentamycin added up to 30 micrograms per ml and mixtures thereof. A mixture of thimerosal (preferably in a 1:10,000 final concentration) and gentamicin (30 microgram/ml) is preferred.

The cultures may be adjuvanted in accordance with techniques known to those in the art with any of the known adjuvants. Examples of suitable adjuvants include: any of the carbopol-based, oil-based and aluminum based adjuvants which are commercially available. 10% aluminum hydroxide gel is particularly preferred.

BPL inactivated cultures of virulent $F.$ $necrophorum$ isolates may then be combined with an adjuvant to prepare final bacterin.

The bacterin of the present invention may be administered to any of the ruminant animals such as cattle or sheep by any of the known procedures or a combination of the known procedures for parenteral administration such as intramuscular or subcutaneous injection. In most cases, intramuscular injection is preferred. The appropriate dosage of bacterin will, of course be dependent upon the size of the animal being treated and may be readily determined by the administering veterinarian. It has been found, however, that a dose of from about 1 to about 4 ml is generally suitable for adult sheep and a dose of from about 2 to about 6 ml is generally suitable for adult cattle.

It is also preferable to administer the bacterin in a series of doses, preferably in a series of from about 2 to about 3, preferably about 2 injections which are given at intervals of from about 2 to about 6 weeks, preferably from about 3 to about 5 weeks. The bacterins of the present invention which were prepared from isolates 5118 and 5120 have been found to provide very good protection of cattle and sheep from fusobacterium disease after two intramuscular injections given at intervals ranging from 2 to 6 weeks.

Having thus described my invention in detail, the following Examples are given as being illustrative thereof. All percentages given in these Examples are percentages by weight, unless otherwise indicated.

EXAMPLES

Example 1

The following is a description of methodology used to prepare $F.$ $necrophorum$ Experimental Serial X0188. This serial was used to vaccinate cattle in the South Dakota Cattle Efficacy Trial the results of which are reported in Table 1.

Frozen seed cultures of $F.$ $necrophorum$ isolates 5118 and 5120 were inoculated onto blood agar plates prepared from brain heart infusion agar, 5% bovine blood, and 0.05% l-cysteine-HCl. These cultures were incubated in an anaerobic glove box at 37° C. for approximately 24 hours under an atmosphere of 80% $N_2$, 10% $H_2$, and 10% $CO_2$. A sample of the bacterial lawn from the blood agar plates was transferred using an inoculating loop into 125 ml bottles of Eugon Broth (which is commercially available from Baltimore Biological Laboratories (BBL)) supplemented with 0.5% maltose, 0.5% Beef Extract (available from BBL), 0.5% Yeast Extract (available from BBL), 50 milligram/l hemin, 500 microgram/l menadione, 0.05% l-cysteine hydrochloride.

The culture bottles were incubated at 37° C. in an anaerobic glove box for approximately 24 hours at which time the contents were used to inoculate 1500 ml flasks of Brain Heart Infusion Broth (BHI) supplemented with 1% yeast extract and 0.05% l-cysteine-HCl. Flasks were incubated at 37° C. in the glove box for approximately 18 hours by which time the fermentation was complete. The flasks were then chilled to approximately 4° C. in a refrigerator.

β-propiolactone (0.11% v/v) was added to each flask and each flask was then mixed to distribute the inactivating agent evenly. The flasks were then stored at 4° C. After 4 days, the BPL was hydrolyzed by heating the cultures to 37° C. for 3 hours in a water bath. To test for inactivation, samples from each of the inactivated cultures were streaked on BHI blood agar plates and incubated anaerobically for 24 hours. No growth was observed on the plates. An experimental bivalent bacterin was prepared by combining volumes of the 5118 and 5120 inactivated cultures in a 1:1 ratio, then adjuvanting with 10% aluminum hydroxide gel (Rehydrogel, Reheis Chemical Company). Gentamicin (30 microgram/ml) was added as a preservative.

The Bivalent $F.$ $necrophorum$ bacterin Serial X0188 prepared as described above was tested under field conditions to determine its efficacy in reducing Acute Bovine foot rot in feedlot cattle. Approximately 1500 non-breeding cattle, steers or heifers, at a South Dakota feedlot were used in the trial. Cattle were grouped in 12 pens. Approximately half the cattle in each pen were randomly assigned as vaccinates and received two 5 ml intramuscular injections, 3 weeks apart, with $F.$ $necrophorum$ Serial X0188. Remaining cattle were assigned as controls and received two 5 ml vaccinations with placebo (aluminum hydroxide adjuvanted BHI media). Cattle were observed for cases of Acute Bovine foot rot over a 6 month period. Results of the trial are summarized in Table 1. Twenty-six of 783 control cattle (3.3%) developed cases of acute foot rot during the course of the trial, all of which were subsequently treated with antibiotics (sulfonamide drugs). Three of the 26 cattle did not respond to treatment. These cattle developed cases of chronic foot rot and had to be culled from the herd and shipped for slaughter. Eleven of 763 vaccinated cattle (1.4%) developed cases of acute foot rot, all of which responded to treatment with antibiotics. Relative incidence of foot rot among vaccinates and controls was statistically different (P<0.05) based upon Chi-Square Analysis. Results were also evaluated based upon a clinical index which takes into account the increased severity of disease seen in affected controls. A 64.1% reduction in clinical index was observed among vaccinated cattle.

In summary, vaccination resulted in a statistically significant reduction in incidence of acute foot rot in feedlot cattle and also showed signs of reducing severity of disease. Results show that the BPL inactivated *F. necrophorum* bacterin is efficacious against foot rot in cattle under normal field conditions.

TABLE 1

*F. NECROPHORUM* FEEDLOT CATTLE EFFICACY RESULTS

| | No. Cattle | No. Cases Acute Foot Rot | Percent*** Incidence | % Reduction Incidence | No. Cases Chronic Foot Rot | Clinical Index (CI) | % Reduction In CI |
|---|---|---|---|---|---|---|---|
| Vaccinated Cattle* | 763 | 11 | 1.4% | 57.6% | 0 | 0.28 | 64.1% |
| Control Cattle** | 783 | 26 | 3.3% | — | 3 | 0.78 | — |

*Vaccinated cattle received two 5 ml intramuscular dose of *F. necrophorum* Bacterin Experimental Serial X1088.
**Control Cattle received two 5 ml intramuscular dose of Placebo.
***Relative incidence of foot rot among vaccinates and controls was statistically different (P < .05) based upon Chi-Square Analysis.

Example 2

The following methodology was used to prepare *F. necrophorum* Experimental Serials 29687BB and X0988. These serials were used to vaccinate sheep in the Sheep Efficacy Trials summarized in Tables 2, 3 and 4. The only differences between Serials 29687BB and X0988 were due to use of different experimental lots of *F. necrophorum* 5118 and 5120 in each serial.

Frozen seed cultures of *F. necrophorum* isolates 5118 and 5120 were inoculated onto blood agar plates prepared from brain heart infusion broth, (Difco), 1% yeast extract (Yeast Products, Inc.), 0.05% purified Agar (Difco), 5% fresh bovine blood and 0.05% l-cysteine HCl. Following 24 hours incubation at 37° C. in an anaerobic glove box under a gaseous atmosphere of 10% hydrogen, 10% carbon dioxide, and 80% nitrogen, loopfuls of colonial growth were transferred from blood plates to tubes containing 15 ml of BHI broth supplemented with 1% yeast extract and 0.05% l-cysteine HCl. The tubes were incubated anaerobically at 37° C. for approximately 8 hours. 3 ml volumes of active seed culture were then passaged into bottles containing 80 ml of Brain Heart Infusion Broth (BHI) supplemented with 1% yeast extract and 0.05% l-cysteine-HCl and incubated anaerobically at 37° C. Following 16 to 18 hours incubation, cultures were passaged again, this time into 350 ml of the Brain Heart Infusion Broth supplemented with 1% yeast extract and 0.05% l-cysteine HCl and incubated anaerobically at 37° C. for approximately 8 hours.

Finally 10 liter volumes of BHI-yeast media supplemented with 0.05% l-cysteine HCl were inoculated with active seed culture (3.5% to 4.5% v/v) and incubated at 37° C. with constant mixing for approximately 16 hours. Cultures were chilled to 40° C. in an ice bath, inactivated with β-propiolactone (0.11%), and mixed at 4° C. for 4 days. Residual BPL was hydrolyzed by heating the cultures at 37° C. for 4 hours. Hydrolyzed cultures were tested for inactivation in the same manner as was described in Example 1. Samples were streaked on BHI blood agar plates and incubated anaerobically for 24 hours. No growth was observed on the plates.

Inactivated cultures of 5118 and 5120 were adjuvanted individually with aluminum hydroxide gel (10% v/v) and preserved with gentamicin (30 microgram/ml). A bivalent bacterin was prepared by combining equal volumes of inactivated, adjuvanted 5118 and 5120 cultures.

Bivalent *F. necrophorum* bacterins 29687BB and X0988 prepared as described above were tested in Oregon sheep herds having histories of chronic foot rot to determine their effectiveness in reducing *F. necrophorum* disease. Sheep used in Trial 1 were pregnant ewes, two years and older of Suffolk or Suffolk-Dorset cross breeds. Sheep used in Trials 2 and 3 were young ewes, one to two years of age. Sheep were allowed to roam free on pasture but were supplemented with a free choice mineral supplement containing sodium chloride, calcium, phosphorus, magnesium, manganese, iodine, iron, cobalt, zinc, selenium, Vitamin A, Vitamin D3, Vitamin E and Lasalocid, an ionophore used as a coccidiostat.

Sheep were randomly assigned to either vaccinate or control groups. Vaccinates received two 3 ml intramuscular vaccinations 5 weeks apart with bivalent *F. necrophorum* bacterins 29687BB or X0988. Controls received two 3 ml vaccinations with a placebo (BHI media adjuvanted with aluminum hydroxide gel).

At the time of initial vaccination (T1), individual feet of all vaccinated and control sheep were evaluated and given an individual foot score using a clinical index based upon a scale provided by Dr. John Berg, University of Missouri, Columbia, Mo. Five months later (T2), individual feet of vaccinate and control sheep were again examined and scored. The difference in Clinical Index between Time T1 and T2 reflects the progress of *F. necrophorum* disease on a "per foot" basis. The total numbers of feet tested were slightly different for vaccinated and control sheep. In addition to slight variance in numbers of vaccinates and controls, a certain number of feet were not included in the study. These feet were already in an advanced state of chronic disease at time of initial vaccination and were not suitable for evaluation in these trials.

| Clinical Index for Evaluation of Footrot in Sheep | |
|---|---|
| Clinical Sign | Score |
| I. No Visible Lesion | 0 |
| II. Lesions Involving interdigital space | |
|    A. Interdigital dermatitis | 2 |
|    B. Interdigital dermatitis with significant inflammation | 3 |
|    C. Interdigital dermatitis with very severe inflammation | 4 |
| III. Lesions involving breakdown of the horn | |
|    A. Undermining of horn, sole, wall at the heel - no necrosis | 1 |
|    B. Undermining of horn at the heel with necrosis, odor | 3 |
|    C. Undermining of sole - no necrosis | 2 |
|    D. Undermining of sole with necrosis, odor | 4 |
|    E. Undermining of the wall - no necrosis | 2 |
|    F. Undermining of the wall with necrosis, odor | 4 |

Results of the three sheep trials are summarized in Tables 2, 3, and 4. Acute Ovine foot rot increased substantially among control sheep in each of the trials. Vaccinated sheep which received *F. necrophorum* Bacterins 29687BB or X0988 showed significant reductions in disease ranging from 61.2% (Trial 1) to 87.9% (Trial 3) when compared to controls. The overall reduction In Clinical Index for all 2424 feet evaluated In the 3 trials was 80.0%. The difference In Mean Clinical Indices between vaccinated and control sheep was shown to be statistically significant ($P<0.01$) for each of the three individual trials using Student's t Test.

Results of these studies showed a significant reduction in fusobacterium disease among vaccinated sheep and demonstrated the efficacy of BPL inactivated bacterin under field conditions.

TABLE 2

*F. NECROPHORUM* SHEEP EFFICACY TRIAL NO. 1
NUMBER OF FEET SHOWING INDICATED CHANGE IN CLINICAL INDEX (ACI)
(BETWEEN INITIAL AND FINAL OBSERVATIONS

| | ACI | | | | | | | | TOTAL | TOTAL | MEAN CLINICAL INDEX |
|---|---|---|---|---|---|---|---|---|---|---|---|
| | -4 | -3 | -2 | -1 | 0 | 1 | 2 | 3 | 4 | SCORE | NO. FEET | (MCI)*** |
| *Vaccinated Sheep (N-94) | 1 | 0 | 63 | 4 | 154 | 9 | 39 | 17 | 19 | 80 | 306 | 0.26 |
| **Control | 0 | 0 | 52 | 5 | 149 | 5 | 46 | 35 | 31 | 217 | 323 | 0.67 |

*Vaccinated Sheep received two 3 ml intramuscular dose of *F. Necrophorum* Bacterin Experimental Serial 2968188.
**Control Sheep received two 3 ml intramuscular dose of Placebo.
***Mean Clinical Index (MCI) - Total Score/Total No. Feet. The MCIs of vaccinated and control sheep were shown to be statistically different ($P < .01$) using Students t Test.

TABLE 3

*F. NECROPHORUM* SHEEP EFFICACY TRIAL NO. 2
NUMBER OF FEET SHOWING INDICATED CHANGE IN CLINICAL INDEX (ACI)
(BETWEEN INITIAL AND FINAL OBSERVATIONS

| | ACI | | | | | | | | | TOTAL | TOTAL | MEAN CLINICAL INDEX |
|---|---|---|---|---|---|---|---|---|---|---|---|---|
| | -4 | -3 | -2 | -1 | 0 | 1 | 2 | 3 | 4 | SCORE | NO. FEET | (MCI)*** |
| *Vaccinated Sheep (N-103) | 2 | 13 | 1 | 7 | 267 | 2 | 42 | 7 | 5 | 71 | 346 | 0.21 |
| **Control Sheep (N-95) | 2 | 3 | 2 | 7 | 150 | 7 | 83 | 29 | 54 | 488 | 337 | 1 33 |

*Vaccinated Sheep received two 3 ml intramuscular doses of *F. Necrophorum* Bacterin Experimental Serial X0988.
**Control Sheep received two 3 ml intramuscular doses of Placebo.
***Mean Clinical Index (MCI) = Total Score/Total No. Feet. The MCIs of vaccinated and control sheep were shown to be statistically different ($P < .01$) using Students t Test.

TABLE 4

F. NECROPHORUM SHEEP EFFICACY TRIAL NO. 3
NUMBER OF FEET SHOWING INDICATED CHANGE IN CLINICAL INDEX (ACI)
(BETWEEN INITIAL AND FINAL OBSERVATIONS

| | ACI | | | | | | | | | TOTAL | TOTAL | MEAN CLINICAL INDEX |
|---|---|---|---|---|---|---|---|---|---|---|---|---|
| | −4 | −3 | −2 | −1 | 0 | 1 | 2 | 3 | 4 | SCORE | NO. FEET | (MCI)*** |
| *Vaccinated Sheep (N-144) | 9 | 15 | 28 | 4 | 447 | 2 | 42 | 5 | 16 | 24 | 568 | 0.04 |
| **Control Sheep (N-137) | 8 | 8 | 18 | 3 | 395 | 5 | 72 | 13 | 22 | 181 | 544 | 0.33 |

*Vaccinated Sheep received two 3 ml intramuscular doses of *F. Necrophorum* Bacterin Experimental Serial X0988.
**Control Sheep received two 3 ml intramuscular doses of Placebo.
*** Mean Clinical Index (MCI) - Total Score/Total No. Feet. The MCIs vaccinated and control sheep were shown to be statistically different (P < .01) using Students t Test.

Example 3

Monovalent *F. necrophorum* 5118 and 5120 bacterins were prepared in the same manner using the same materials as were described in Example 1. Mouse challenge trials were conducted to determine whether the experimental monovalent bacterins could protect mice from virulent challenge with heterologous isolates of *F. necrophorum*. Virulent *F. necrophorum* isolates 5103, 5116, and 5120 were obtained from cases of ovine foot rot in 3 different Missouri sheep herds. Isolate 2382 was a bovine Liver Abscess isolate obtained from a calf slaughtered at a Missouri Packing Plant. Each of these isolates exhibited typical colonial morphology, mouse pathogenicity and microscopic characteristics of *F. necrophorum*. Groups of five or ten 18 to 20 gram Swiss-Webster mice received three 0.2 ml subcutaneous injections of either 5118 bacterin or 5120 bacterin at weekly intervals. Equal numbers of control mice received 0.2 ml SC of placebo (adjuvanted PBS). One week post final vaccination, groups of vaccinate and control mice were challenged intraperitoneally with 0.25 ml of 16 hour cultures of either *F. necrophorum* isolate 5103, 5116, 5120, or 5126.

Mice were observed and deaths recorded over a 7 day observation period. Results of the mouse challenge trials are presented In Table 5.

Results showed that monovalent bacterins prepared from *F. necrophorum* isolates 5118 and 5120 could protect mice from lethal challenge. It was significant that protection was seen against a variety of heterologous isolates. Thus, β-propriolactone inactivated isolates 5118 and 5120 bacterins appear to provide effective protective immunity under field conditions.

TABLE 5

Mouse Challenge Trials Using *F. necrophorum*
5118 and 5120 Monovalent Bacterins
(Results Expressed as Survivors/Total)

| Monovalent Bacterin | Challenge Isolates FN 5103 [Ovine] | FH5116 [Ovine] | FN5126 [Ovine] | FN2382 [Bovine] |
|---|---|---|---|---|
| 5118 | 9/10 | 9/10 | 8/10 | 5/5 |
| 5120 | 10/10 | 7/10 | 8/9 | 8/10 |
| PBS PLACEBO | 0/10 | 1/10 | 0/10 | 3/10 |

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A method for treating cattle and sheep to prevent foot rot or liver necrosis comprising administering a *Fusobacterium necrophorum* bacterin, which is a β-propriolactone inactivated *Fusobacterium necrophorum* isolate, and an adjuvant to the animal being treated in an effective combination that protects against foot rot or liver necrosis.

2. The method of claim 1 in which the bacterin also includes an adjuvant.

3. The method of claim 2 in which the bacterin has been treated to remove any residual β-propriolactone present.

4. The method of claim 1 in which the bacterin has been treated to remove any residual β-propriolactone present.

5. The method of claim 1 in which the bacterin is administered parenterally to the animal being treated.

6. The method of claim 5 in which the bacterin is administered to the animal being treated in a series of at least two injections.

7. The method of claim 1 in which the bacterin is administered to the animal being treated by subcutaneous injection.

8. The method of claim 7 in which the bacterin is administered to the animal being treated in a series of at least two injections.

9. A method for treating cattle and sheep to prevent foot rot or liver necrosis comprising administering a *Fusobacterium necrophorum* vaccine comprising a β-propriolactone inactivated *Fusobacterium necrophorum* isolate and an adjuvant, to the animal being treated.

10. The method of claim 9 wherein the *Fusobacterium necrophorum* isolate is free of contamination with red blood cells.

* * * * *